(12) United States Patent
Korkosz et al.

(10) Patent No.: US 6,262,659 B1
(45) Date of Patent: Jul. 17, 2001

(54) TELEMETRY OF DIAGNOSTIC MESSAGES FROM A MOBILE ASSET TO A REMOTE STATION

(75) Inventors: Richard August Korkosz, Rotterdam Junction, NY (US); William Robert McKinney, Sr.; Bruce Gunther Schings, both of Loveland, OH (US); John Anderson Fergus Ross, Latham, NY (US); Naofal Mohammed Wassel Al-Dhahir, Niskayuna, NY (US); Harold Woodruff Tomlinson; Charles McDonald Puckette, both of Scotia, NY (US); John Erik Hershey, Ballston Lake, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/260,707

(22) Filed: Mar. 2, 1999

Related U.S. Application Data

(60) Provisional application No. 60/076,666, filed on Mar. 3, 1998, and provisional application No. 60/076,610, filed on Mar. 3, 1998.

(51) Int. Cl.[7] .................................................. G08B 1/08
(52) U.S. Cl. ................... 340/539; 340/870.07; 340/945; 701/14; 375/130; 455/66; 455/67.1
(58) Field of Search .............................. 340/539, 870.07, 340/870.01, 945; 455/66, 67.1, 54.1, 33.1; 701/14, 35; 375/200, 219, 130

(56) References Cited

U.S. PATENT DOCUMENTS

| | | | |
|---|---|---|---|
| 4,642,775 | * | 2/1987 | Cline et al. ............................ 364/443 |
| 4,729,102 | * | 3/1988 | Miller, Jr. et al. ...................... 369/21 |
| 5,065,321 | | 11/1991 | Bezos et al. ..................... 340/870.41 |

(List continued on next page.)

FOREIGN PATENT DOCUMENTS

| | | |
|---|---|---|
| 0 249 487 | 12/1987 | (EP) . |
| 0 292 811 | 5/1988 | (EP) . |
| 2 693 068 | 6/1992 | (FR) . |

OTHER PUBLICATIONS

"Wireless LAN Data Alternatives," DF Bantz, FJ Bauchot, IEEE Network, Mar./Apr. 1994, pp. 43–53.

"Reliable Wireless Telephony Using the 2.4 GHz ISM Band: Issues and Solutions," Proceedings of ISSSTA '95 International Symposium on Spread Spectrum Techniques and Applications Proceedings, 1996, vol. 2, pp. 790–794.

"Diversity Performance of Direct Sequence Spread Spectrum ISM Band Radio LANs in Multipath Channels," TA Wilkinson; SK Barton, IEE Colloquium on 'Spread Spectrum Techniques for Radion Communication Systems,' 1994, pp. 12/1–12/6.

CCIR Report 721–5, Figure 1, p. 200, vol. V, XVIth Plenary Assembly, Dubrovnik, 1986.

"Fig. 12.4 Typical Operating Noise Factors for Various Radio Noise Sources," from Reference Manual for Telecommunications Engineering, 2nd Edition, R. Freeman, John Wiley & Sons, ©1991.

*Primary Examiner*—Donnie L. Crosland
(74) *Attorney, Agent, or Firm*—Jill M. Breedlove; Douglas E. Stoner

(57) ABSTRACT

A telemeter for telemetry of diagnostic messages from a mobile asset to a remote station comprises a processor coupled to the output of one or more condition sensors. The processor converts the output of the condition sensors to a diagnostic message, and provides the diagnostic message at a processor output. A transmitter is coupled to the processor output. The transmitter is adapted to transmit the diagnostic messages in the Industrial, Scientific, Medical (ISM) frequency band. An exemplary embodiment of a telemetry system of the invention comprises a telemeter adapted to transmit diagnostic messages in the ISM frequency band, and a remote station including a receiver for receiving the diagnostic messages in the ISM band.

17 Claims, 6 Drawing Sheets

U.S. PATENT DOCUMENTS 5,459,469 * 10/1995 Schuchman et al. .................. 342/37
5,463,656 * 10/1995 Polivka et al. ....................... 375/200
5,530,909    6/1996 Simon et al. ....................... 455/11.1
6,047,165 *  4/2000 Wright et al. ......................... 455/66

* cited by examiner

| | | |
|---|---|---|
| TRANSMIT POWER (dBm) | 35 | |
| CARRIER FREQUENCY (GHz) | 2.442 | |
| WAVELENGTH (METER) | 0.12285 | |
| TRANSMIT ANTENNA GAIN (dBi) | -2 | |
| TRANSMITTED EIRP (dBm) | 33 | FCC ALLOWS UP TO 36 dBm |
| RANGE (MILES) | 200 | |
| RANGE (Km) | 321.8 | |
| FREE SPACE LOSS (dB) | -150.348 | |
| BOLTZMANN'S CONSTANT | -228.6 | |
| OTHER LINK LOSSES (dB) | -1 | |
| RECEIVE ANTENNA ELEMENT DIAMETER (CM) | 20 | |
| RECEIVE ANTENNA ELEMENT EFFICIENCY | 0.6 | 60% efficiency |
| RECEIVE ANTENNA ELEMENT GAIN (dBi) | 11.95759 | |
| NUMBER OF RECEIVE ARRAY ELEMENTS | 16 | |
| RECEIVE ANTENNA ARRAY GAIN (dBi) | 23.99879 | ARRAY GAIN OF 12 dB |
| RECEIVER NOISE FIGURE (dB) | 3 | |
| RECEIVER NOISE FIGURE (DIMENSIONLESS) | 1.995262 | |
| RECEIVER NOISE TEMPERATURE (K) | 288.6261 | |
| ANTENNA NOISE TEMPERATURE (K) | 100 | TSKY=70  TGND=30 |
| SYSTEM NOISE TEMPERATURE (K) | 388.6261 | |
| SYSTEM NOISE TEMPERATURE (dB.K) | 25.89532 | |
| RECEIVER G/T (dB/K) | -1.89653 | |
| Pr/No (dB/K) | 78.35507 | |
| DATA RATE (kdps) | 1000 | 1 MBPS |
| DATA RATE (dB-kbps) | 30 | |
| IMPLEMENTATION LOSS (dB) | -2 | |
| AVAILABLE Eb/No (dB) | 16.35507 | |
| BIT ERROR RATE | 10^(-5) | |
| MODULATION SCHEME | DQPSK | |
| REQUIRED Eb/No (dB) | 12 | |
| CODING GAIN (dB) | 0 | NO CODING |
| MARGIN (dB) | 4.355072 | | fig. 5

| | | |
|---|---|---|
| TRANSMIT POWER (dBm) | 23 | |
| CARRIER FREQUENCY (GHz) | 2.442 | |
| WAVELENGTH (METER) | 0.12285 | |
| TRANSMIT ANTENNA DIAMETER (cm) | 20 | |
| TRANSMIT ANTENNA EFFICIENCY | 0.6 | 60% EFFICIENCY |
| TRANSMIT ANTENNA GAIN (dBi) | 11.95759 | |
| TRANSMITTED EIRP (dBm) | 34.95759 | FCC ALLOWS UP TO 36 dBm |
| RANGE (MILES) | 200 | |
| RANGE (Km) | 321.8 | |
| FREE SPACE LOSS (dB) | -150.348 | |
| BOLTZMANN'S CONSTANT | 228.6 | |
| OTHER LINK LOSSES (dB) | -1 | |
| RECEIVE ANTENNA GAIN (dBi) | -2 | |
| RECEIVER NOISE FIGURE (dB) | 3 | |
| RECEIVER NOISE FIGURE (DIMENSIONLESS) | 1.995262 | |
| RECEIVER NOISE TEMPERATURE (K) | 288.6261 | |
| ANTENNA NOISE TEMPERATURE (K) | 70 | |
| SYSTEM NOISE TEMPERATURE (K) | 358.6261 | |
| SYSTEM NOISE TEMPERATURE (dB.K) | 25.54642 | |
| RECEIVER G/T (dB/K) | -27.5464 | |
| Pr/No (dB.bps) | 54.66277 | |
| DATA RATE (kdps) | 4.8 | |
| DATA RATE (dB-kbps) | 6.812412 | |
| IMPLEMENTATION LOSS (dB) | -2 | |
| AVAILABLE Eb/No (dB) | 15.85036 | |
| BIT ERROR RATE | 10^(-5) | |
| MODULATION SCHEME | DQPSK | |
| REQUIRED Eb/No (dB) | 12 | |
| CODING GAIN (dB) | 0 | NO CODING |
| MARGIN (dB) | 3.850361 | | fig. 6

TELEMETRY OF DIAGNOSTIC MESSAGES FROM A MOBILE ASSET TO A REMOTE STATION

CROSS REFERENCE TO RELATED APPLICATIONS

This invention claims priority from Provisional Applications Nos. 60/076,666 filed Mar. 3, 1998, and 60/076,610 filed Mar. 3, 1998.

BACKGROUND OF THE INVENTION

This invention relates generally to remote monitoring and diagnostics, and more specifically relates to telemetry of diagnostic messages from a mobile asset to a remote service center. One embodiment of the present invention is a telemetry system employing airborne sensors and telemeters to transmit maintenance data (such as performance data of an aircraft engine) from an aircraft-in-flight to a ground based service center.

Remote monitoring and diagnosing of the condition, performance, and failure of parts, equipment and systems carried by mobile assets such as airplanes, turbines, locomotives and medical systems is becoming increasingly important as industry struggles to improve safety, reduce maintenance costs and deliver efficient, timely and cost effective maintenance services to its customers. For that reason, remote maintenance services are seen by today's service oriented businesses as an important growth area. Remote monitoring and diagnosing capability is quickly becoming a key element in providing high-technology, value-added services for an installed equipment base which equipment base may include mobile assets such as power generation equipment, aircraft engines, medical imaging systems, and locomotives.

By monitoring the performance of such equipment and systems, an indication that a system is malfunctioning can be obtained. By providing diagnostic messages which contain information about a malfunctioning system, a measure of safety is obtained that can be of particular importance in ensuring the system is capable of performing as required. In addition, such information can be utilized to initiate a maintenance cycle before placing the system into a subsequent cycle of operation.

Control systems for devices such as turbines used for generation of electricity or turbines used in aircraft engines typically monitor a variety of turbine performance parameters, including speed, temperatures, and stresses on the turbine assembly. Prior art systems provide for monitoring these parameters in flight. However, many of the problems associated with relaying these parameters to a ground service center while the aircraft is in flight remain to be solved.

A significant problem encountered in the art of wireless digital communications of performance parameters relates to the frequency and, more importantly, the power at which telemetry devices can transmit RF signals. Until the enactment by the Federal Communications Commission (FCC) of Part 15.247 of the FCC Rules and Regulations, aircraft telemetry systems were primarily limited to the VHF band (174–216 MHz), and could only operate at very low transmission powers of less than 0.1 milliwatts (mW). (See FCC Part 15.241.) This restriction on the transmission power has significantly limited the transmission range (i.e., the maximum distance between the transmitter and the receiver) of airborne telemetry devices. Restrictions also place limits on the data rate or "bandwidth" at which the telemetry devices can transmit data.

Because of these factors the frequency bands available for transmission of information from an aircraft to ground, and vice versa, is limited. Further, there are increasing demands for other types of communications, such as voice, to utilize these available regulated bands. Adding diagnostic information channels often requires modifications to the airframe of the aircraft to add additional antennas. Because of the cost of these structural modifications, and the high recurring cost of acquiring transmission time for relaying flight performance data in the regulated frequency bands, there is a pressing need for improved systems and methods for transmitting aircraft diagnostic information from an aircraft to a ground station.

SUMMARY OF THE INVENTION

In an exemplary embodiment of the invention, a telemeter comprises a processor coupled to the output of one or more condition sensors. The processor converts the output of the condition sensors to a diagnostic message, and provides the diagnostic message at a processor output. A transmitter is coupled to the processor output. The transmitter is adapted to transmit the diagnostic messages in the Industrial, Scientific, Medical (ISM) frequency band. An exemplary embodiment of a telemetry system of the invention comprises a telemeter adapted to transmit diagnostic messages in the ISM frequency band, and a remote station including a receiver for receiving the diagnostic messages in the ISM band.

An exemplary embodiment of a method of the invention includes the steps of 1) collecting performance information from a mobile asset, 2) transmitting the performance information to a remote station via an ISM band transmission, 3) receiving the mobile asset performance information at a remote station, and 4) utilizing the asset performance information.

BRIEF DESCRIPTION OF THE DRAWINGS

FIG. 5 shows exemplary specifications for a mobile asset to remote station link according to one embodiment of the present invention.

FIG. 6 shows exemplary specifications for a ground station to mobile asset link according to one embodiment of the present invention.

DETAILED DESCRIPTION OF THE INVENTION

Figure 1:
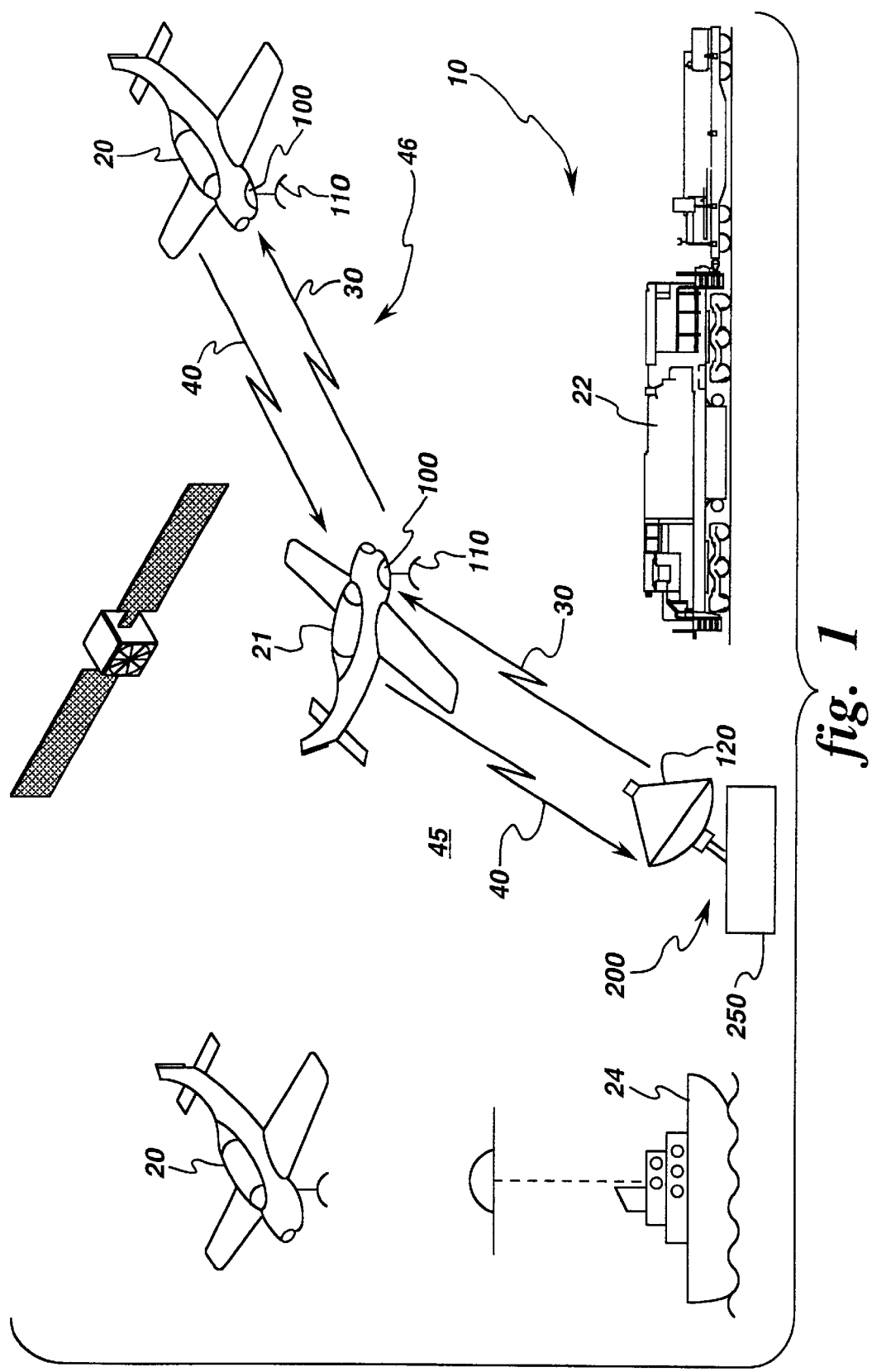
FIG. 1 is a pictorial block diagram of a telemetry system according to one embodiment of the present invention.

A telemetry system 10 according to one embodiment of the present invention is illustrated in FIG. 1. Telemetry system 10 comprises a telemeter 100, a transmitter 118 and a remote station 200. Telemeter 100 is carried upon a mobile asset, such as an aircraft 20, locomotive 22, ship 24, or the like and configured to monitor the condition of the asset upon which it is installed. Telemeter 100 in conjunction with transmitter 118 transmits messages, referred to herein as diagnostic messages, containing information about the condition and performance of the assets to remote station 200. The term "condition" refers to the state of readiness, or fitness for operation of an asset or of a particular component of an asset.

According to one embodiment of the invention, diagnostic messages are relayed directly from the asset, such as aircraft 20, being monitored (referred to herein as a source) to a remote station 200 (referred to herein as a destination). According to another embodiment of the present invention diagnostic messages are relayed in series from a source asset, such as aircraft 20, to a successor asset, such as aircraft 21, and in some cases from a successor asset to another successor asset, and so on until the diagnostic message arrives at its remote station destination 200.

Figure 7:
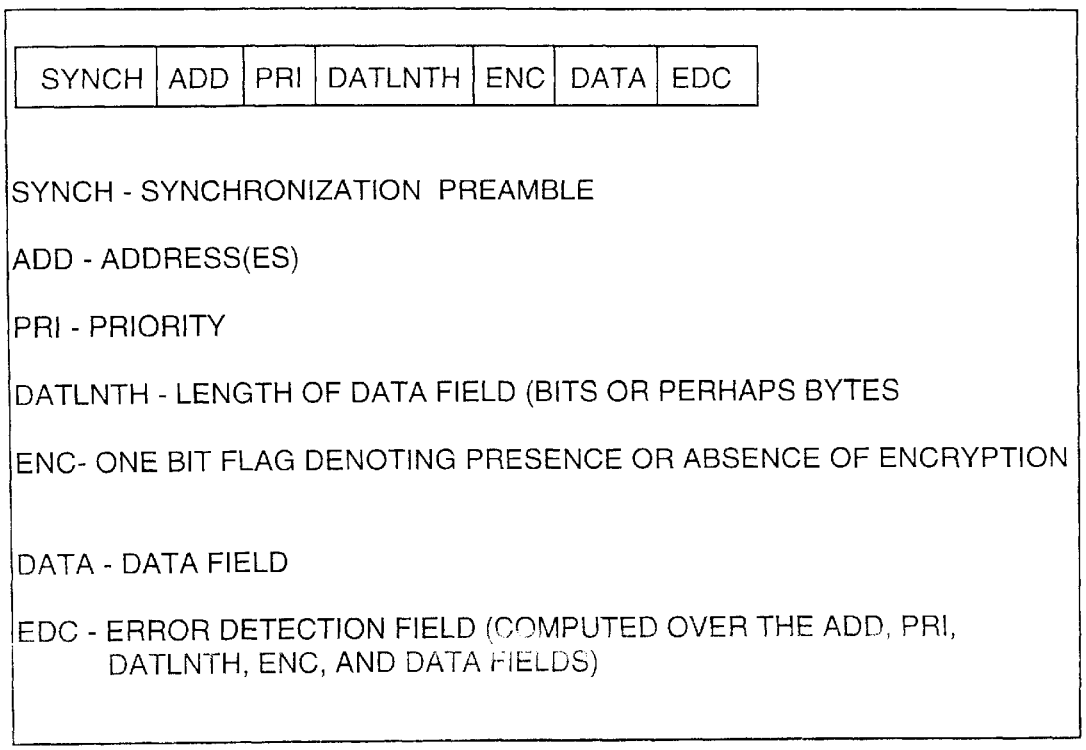
FIG. 7 shows an example diagnostic message format according to one embodiment of the invention.

An exemplary format suitable for diagnostic messages is illustrated in FIG. 7. The message format comprises a synchronization preamble, address bits, priority bits if desired, a data field, an encryption flag denoting the presence or absence of encryption of the data in the data field, and an error detection field.

Diagnostic messages are relayed between source assets, successor assets and remote station destinations via down links 45. Down links 45 according to the present invention are communications channels comprising unlicensed, or Industrial/Scientific/Medical (ISM) band, transmissions. Three ISM bands are now available in the United States for using spread-spectrum communications techniques: 902–928 MHz; 2400–2483.5 MHz; and 5725–5850 MHz.

Accordingly, transmitter 110, according to one embodiment of the invention, is adapted to transmit in an ISM frequency band. In one embodiment of the present invention data links 45 further include non ISM band radio frequency channels such as those licensed by the Federal Communications Commission (FCC).

In one embodiment of the present invention telemeter 100 is installed upon aircraft 20. Telemeter 100 monitors one or more jet engine conditions of aircraft 20 and transmits messages containing information about the performance of the aircraft between aircraft 20 and remote station 200. Remote station 200 utilizes the information contained in the messages to assess engine performance, identify and predict failure conditions, and in one embodiment to relay corrective signals to aircraft 20 via data uplink 30 to correct or compensate for failure conditions. In one embodiment of the invention data uplink 30 comprises ISM band transmissions. In another embodiment of the invention data uplink 30 comprises commands and data in an FCC licensed radio frequency band.

As will be readily understood by those skilled in the art, the invention is not limited to aircraft telemeters and remote stations. Rather, the telemeters of the present invention may be installed upon any mobile asset, and the messages relayed to a remote station, such as a satellite, shipboard or other receiving station which is not ground based.

Figure 2:
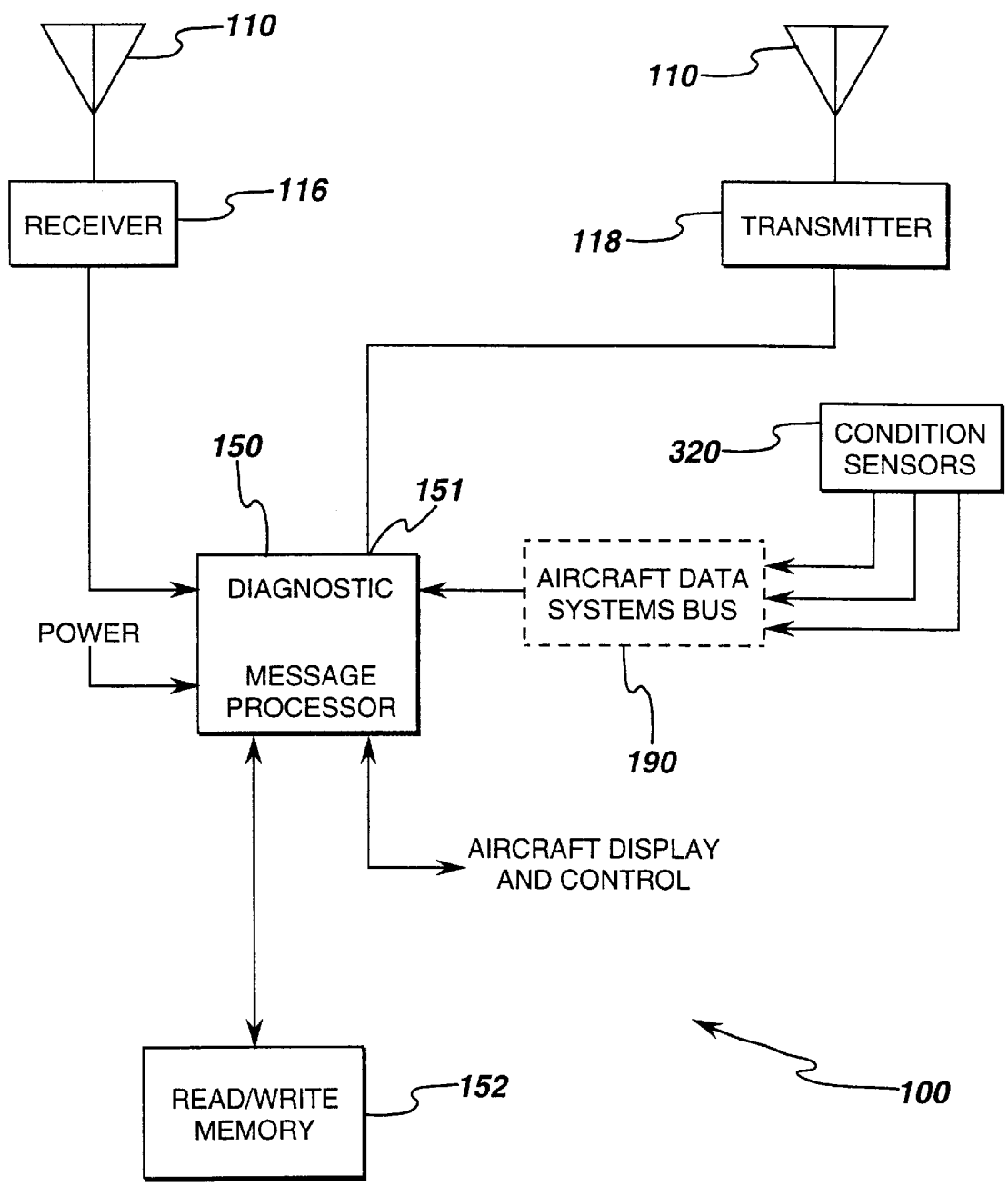
FIG. 2 is a block diagram of a telemeter according to one embodiment of the present invention.

A telemeter 100 according to an embodiment of the invention is illustrated in block diagram form in FIG. 2. Telemeter 100 comprises as major components transmitter 118, receiver 116, diagnostic message processor 150, memory 152, display 190, and condition sensors 320, as shown in FIG. 2. Condition sensors 320 monitor performance conditions and parameters such as turbine speed, and exhaust gas temperature.

In one embodiment of the invention telemeter 100 is implemented using avionics equipment already in place on aircraft 20, as for example VHF, or UHF transceivers for other avionics applications licensed by the FCC for operation in RF bands. For example, Very High Frequency (VHF) transceiver units, not used over oceans where there is no line of sight to a ground station, may be employed to transmit and receive diagnostic messages on unlicensed bands during periods when these VHF transceivers are inactive. In one embodiment of the invention transmitter 118 includes an ISM modem of a type readily commercially available.

In one embodiment of the present invention, telemeter 100 includes a low power 2.4 GHZ ISM transceiver, represented in FIG. 2 by receiver 116 and transmitter 118. Receiver 116 and transmitter 118 include modems employing typical direct sequence spread spectrum modulation schemes to modulate a carrier with diagnostic message information. Such schemes may be implemented in synchronous mode or in transmitted reference mode to alleviate the synchronization overhead.

The ISM band embodiment of the present invention relies on in-flight use of the 2.4 GHz ISM at 2.4 GHz–2.4835 GHz. Commercially available chip sets such as the Harris PRISM™ chip set and a wide variety of support electronics are readily commercially available for use in this embodiment. For example, one embodiment of the invention employs Direct Sequence Spread Spectrum (DSSS) techniques to maintain a spreading factor of at least 10, as required by United States FCC regulations. The Harris PRISM set spreads with a factor of 11 and is programmable for up to a factor of 16, making it advantageous for use in implementing an embodiment of the present invention. An alternative embodiment of the present invention employs 5.7 GHz band transceivers.

Table 1 shows exemplary link specifications developed by simulating an asset-to-asset link according to one embodiment of the present invention. According to the example shown in Table 1, an airplane to airplane link in the 2.4 GHz ISM band between two aircraft, each at a minimum cruise altitude of 20,000 feet and separated by a line of sight distance of about 400 miles will support about a 1.2 kilobit per second link between the two aircraft, without coding, at a bit error rate of no greater than $10^{-5}$. In an alternative embodiment of the present invention the link is operated at a variable data rate depending on the available link margin. In that case, both ends of the link are configured to observe the received error rates, calculated over groups of known bits or by observing various check sum failure rates, and increase or decrease their signaling rates accordingly.

TABLE 1

| Parametdr | Value | Remarks |
|---|---|---|
| Transmit Power (dB) | 36 | |
| Carrier Frequency (GHz) | 2,442 | |
| Wavelength (meter) | 0.12285 | |
| Transmit Antenna Gain (dBi) | −2 | |
| Transmitted EIRP (dBm) | 34 | FCC allows up to 36 dBm |
| Range (miles) | 400 | |
| Tange (Km) | 643.6 | |
| Free Space Loss (dB) | −156.369 | |
| Boltzmann's Constant | −22.86 | |
| Other Link Losses (dB) | −1 | |
| Receive Antenna Element Gain (dB) | −2 | |
| Receiver Noise Figure (dB) | 3 | |
| Receiver Noise Figure (dimensionless) | 1.995262 | |
| Receiver Noise Temperature (K) | 288.6261 | |
| Antenna Noise Temperature (K) | 70 | |
| System Noise Temperature (K) | 358.6261 | |
| System Noise Temperature (dB.K) | 25.54642 | |

TABLE 1-continued

| Parametdr | Value | Remarks |
|---|---|---|
| Receiver G/T (dB/K) | −27.5464 | |
| Pr/No (dB.bps) | 47.68458 | |
| Data Rate (kbps) | 1.2 | |
| Data Rate (db-kbps) | 0.791812 | |
| Implementation Loss (dB) | −2 | |
| Available Eb/No (dB) | 14.89277 | |
| Bit Error Rate | 10^(−5) | |
| Modulation Scheme | DQPSK | |
| Required Eb/No (dB) | 12 | |
| Coding Gain (dB) | 0 | NO CODING |
| Margin (dB) | 2.89277 | |

FIG. 5 shows exemplary link specifications for an asset to remote station link wherein the remote station is a ground based station.

FIG. 6 shows exemplary link specifications for a remote station to asset link wherein the remote station is a ground station and the asset is an aircraft.

Telemeter 100 also includes read/write memory 152. Read/write memory 152, which is dynamic random access memory in one embodiment of the present invention, performs storage of incoming messages for retransmission and keeps a history of system performance measures. System performance measures include, but are not limited to, measures selected from the group comprising: number and size of messages successfully received, number of messages successfully transmitted, latency time distribution, i.e., a histogram of the times that the successfully received messages were stored by the receiving aircraft before they were successfully retransmitted, link quality indicators such as signal to noise estimates, and communications protocol efficiency, e.g. number of transmission retries per message.

A system 100 for telemetry of information from aircraft in flight to a ground station according to one embodiment of the present invention typically comprises a plurality of mobile assets, referred to hereinafter as nodes, in radio communication with each other. Each node may be selected from the group comprising aircraft, land vehicles such as a railroad locomotives, ships, ground transmitting or receiving stations, or communications satellites. Each node is equipped with a telemeter 100 for relaying diagnostic messages between nodes and from a source node to a destination ground station. The source node originates the diagnostic message and determines the most efficient link to the desired destination ground station through intermediate nodes. The source node then transmits the diagnostic message to the first node in the link, that node receives and retransmits the diagnostic message to the next mode in the link, etc. until the message is finally received by the desired ground station. In this manner the aircraft pass the data by relay between aircraft in mutual line of sight such that the data is efficiently migrated from the source node to the ground station. According to one embodiment of the invention, remote station 250 employs a phased array antenna that has a line of sight to aircraft at cruise altitude.

In order to establish an efficient link, the source node, and each successive node in the link, must select its successor node such that the message is transmitted from node to node while the successor node is in line of sight with the predecessor node. In one embodiment of the present invention each node's transceiver is provided with flight plan information in order to facilitate the selection of a successor node to which to transmit the diagnostic message. Flight plan information is information related to the altitudes, flight paths, and times for flights of specific aircraft. In one embodiment of the invention flight plan information is obtained from an aircraft tracking services. An example of such a system includes, but is not limited to, AirTrack. Airtrack is a real-time aircraft tracking program available from METSYS Software and Services, Cropton, Pickering, North Yorkshire, Y018 8HL, England. Flight plan data from the database is loaded into the Diagnostic message processor 150 of each aircraft's telemeter 100. Thereafter, processor 100 of the source node selects successors based on the flight plan data and desired destination remote station.

Figure 4:
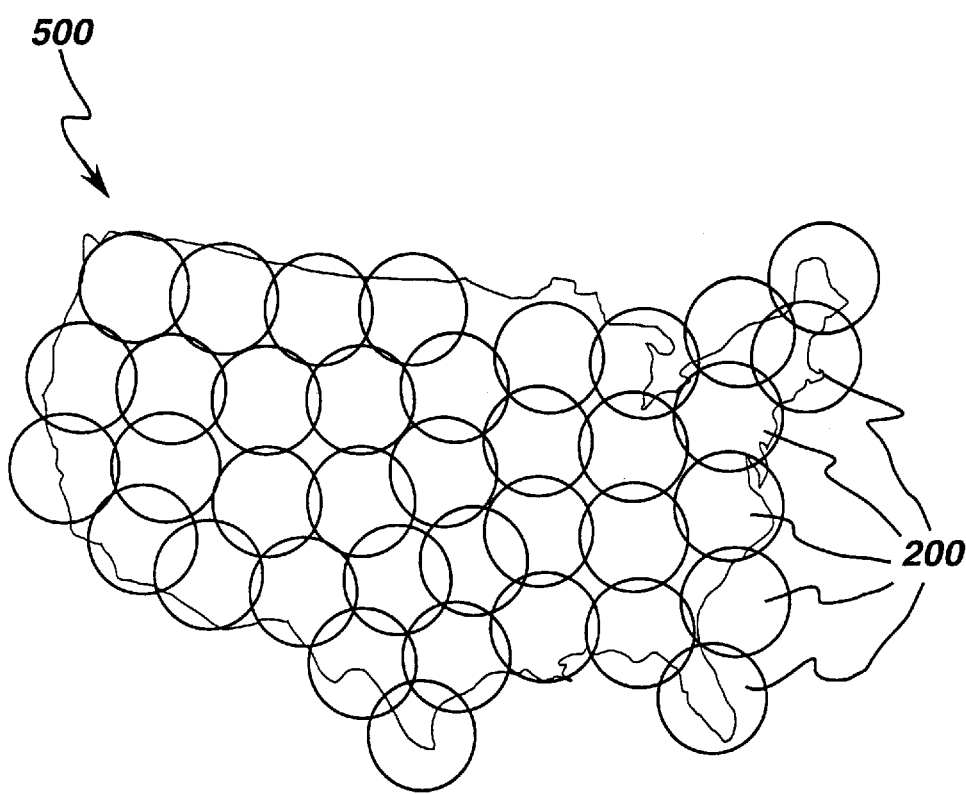
FIG. 4 is a pictorial diagram showing a plurality of remote stations configured in accordance with one embodiment of the present invention.

As shown in FIG. 1, remote station 200 comprises a receiver 250 adapted to receive frequencies in an unlicensed frequency band such as an ISM frequency band. One embodiment of the present invention employs a receiving network 500 comprising several spaced apart remote stations 200 as illustrated in FIG. 4. Remote stations 200 are spaced from each other so as to provide receiver coverage over the entire geographical area of interest 120, in this case the United States, as illustrated in FIG. 4.

Figure 3:
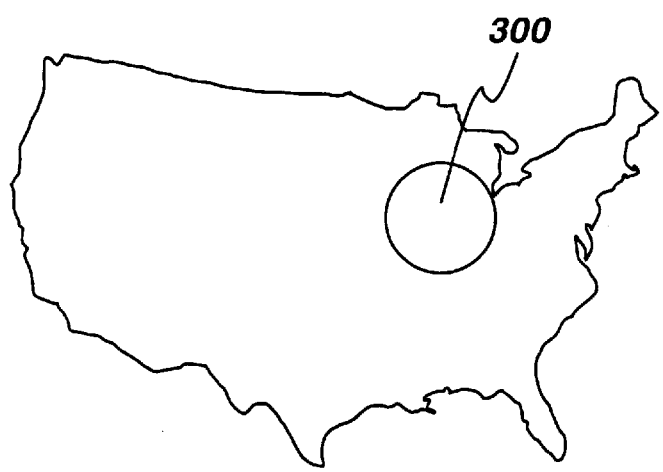
FIG. 3 illustrates an example of a circle of coverage to an aircraft at an altitude of 20,000 ft.

The radio horizon for a line of sight path from an object at H feet above the earth is $\sqrt{2H}$ miles. Thus, a radio receiver on the ground near Evendale, Ohio is capable of line of sight contact with a plane at 20,000 feet whose ground point falls in the circle 300 as shown in FIG. 3. The circle is about 200 miles in radius. For planes at higher altitudes, the circle of coverage expands. FIG. 4 shows a virtual covering of the Continental United States with only 40 receiver sites. A site center is marked with an "x".

The system includes a protocol for fixing and monitoring schedule and performing monitoring hand-off from receiver site to receiver site. The protocol relies upon a ground-to-air link for flow or transmission control including. Examples of ground to air links suitable for transmission control include, but are not limited to: adaptive transmission rate control; provision/non-provision of error correction coding; power control; and time of transmission.

It will be apparent to those skilled in the art that, while the invention has been illustrated and described herein in accordance with the patent statutes, modifications and changes may be made in the disclosed embodiments without departing from the true spirit and scope of the invention. It is, therefore, to be understood that the appended claims are intended to cover all such modifications and changes as fall within the true spirit of the invention.

What is claimed:

1. A telemeter carried on board a mobile asset such as an aircraft, said aircraft having avionics equipment on board for communicating on VHF or UHF bands, said telemeter comprising:

a processor coupled to the output of one or more condition sensors;

said processor configured to convert the output signal of said one or more condition sensors to a diagnostic message, and to provide said diagnostic message at a processor output; and a transmitter coupled to said processor output, said transmitter including circuitry for transmitting said diagnostic message via a spread spectrum signal having a spreading factor of at least about 10 in an Industrial Scientific Medical (ISM) radio frequency band, said transmitter operable while said aircraft is in flight and adapted to utilize said avionics equipment to communicate with a relay station when said avionics equipment is not communicating on VHF or UHF bands.

2. A telemetry system according to claim 1 wherein said transmitter transmits in the 5 GHz band.

3. The telemeter of claim 1 further including a memory 152 for storing diagnostic messages.

4. The telemeter of claim 1 further including:
a receiver coupled to said processor, said receiver configured to receive diagnostic messages transmitted in an Industrial Scientific Medical (ISM) radio frequency band.

5. The telemeter of claim 4 wherein said receiver is further configured to receive commands transmitted from a ground station in a radio frequency band.

6. The telemeter of claim 1 wherein said condition sensor includes an exhaust gas temperature sensor.

7. The telemeter of claim 1 wherein said condition sensor is a turbine speed sensor.

8. The telemeter of claim 1 wherein said processor includes:
a diagnostic message processor comprising:
a message assembler adapted to receive said digital data from said sensor output, and for converting said digital data into one or more diagnostic messages and for providing said diagnostic messages to an assembler output;
a memory for receiving and storing said diagnostic messages from said assembler output and from said receiver; and
a router for directing said diagnostic messages to designated destinations.

9. The telemeter of claim 1 wherein said condition sensor is a core speed sensor.

10. The telemeter of claim 1 wherein said telemeter is carried upon an aircraft.

11. The telemeter of claim 1 wherein said telemeter is carried upon a locomotive.

12. The telemeter of claim 1 wherein said telemeter is carried upon a ship.

13. A telemetry system according to claim 1 wherein said device adapted to utilize said information is a display.

14. A telemetry system according to claim 1 wherein said transmitter transmits electromagnetic energy in the 3.2 GHz ISM Band.

15. A telemetry system comprising:
a telemeter carried on board a mobile asset, said asset having radio communications equipment on board for communicating on VHF or UHF bands, said telemeter including:
an input coupled to the output of one or more condition sensors of said asset;
an output for providing diagnostic messages containing information related to the sensed performance of said asset;
a transmitter having an input coupled to said output of said telemeter, said transmitter including circuitry for transmitting said diagnostic messages in an ISM frequency band via a spread spectrum signal having a spreading factor of at least about 10; and
a remote station comprising:
a receiver for receiving said transmitted messages;
a processor for processing said transmitted messages; and
an output for providing information related to the performance of said asset to a device adapted to utilize said information; said transmitter being adapted to utilize said radio communications equipment to communicate with said remote station when said radio communications equipment is not communicating on VHF or UHF bands.

16. The telemetry system of claim 15 including a plurality of said remote stations configured so as to cover a geographical area of interest.

17. The telemetry system of claim 16 wherein said geographical area of interest is the continental United States.

* * * * *